(12) United States Patent
Sarrafzadeh et al.

(10) Patent No.: US 9,901,815 B2
(45) Date of Patent: Feb. 27, 2018

(54) DEVICES, SYSTEMS, AND METHODS FOR MONITORING, CLASSIFYING, AND ENCOURAGING ACTIVITY

(71) Applicant: The Regents of the University of California, Oakland, CA (US)

(72) Inventors: Majid Sarrafzadeh, Anaheim Hills, CA (US); Jason Holmes, La Canada, CA (US); Jordan Mendler, Tarzana, CA (US); Simran Basi, Pleasanton, CA (US); Diego Villasenor, El Centro, CA (US); Bita Zadeh, Anaheim Hills, CA (US); Daniel Sebastian Pan, Arcadia, CA (US)

(73) Assignee: The Regents of the University of California, Oakland, CA (US)

( * ) Notice: Subject to any disclaimer, the term of this patent is extended or adjusted under 35 U.S.C. 154(b) by 524 days.

(21) Appl. No.: 14/387,225

(22) PCT Filed: Mar. 15, 2013

(86) PCT No.: PCT/US2013/032561
§ 371 (c)(1),
(2) Date: Sep. 22, 2014

(87) PCT Pub. No.: WO2013/142379
PCT Pub. Date: Sep. 26, 2013

(65) Prior Publication Data
US 2015/0050972 A1    Feb. 19, 2015

Related U.S. Application Data

(60) Provisional application No. 61/614,437, filed on Mar. 22, 2012.

(51) Int. Cl.
*A63F 13/212*     (2014.01)
*G06Q 50/10*     (2012.01)
(Continued)

(52) U.S. Cl.
CPC .......... *A63F 13/212* (2014.09); *A61B 5/1118* (2013.01); *A61B 5/6896* (2013.01);
(Continued)

(58) Field of Classification Search
USPC ........................................... 463/7
See application file for complete search history.

(56) References Cited

U.S. PATENT DOCUMENTS

2009/0048526 A1* 2/2009 Aarts ................. A61B 5/02438
600/508
2009/0325701 A1* 12/2009 Andres Del Valle ... A63F 13/12
463/36
(Continued)

FOREIGN PATENT DOCUMENTS

JP     2010-279817 A     12/2010
KR    10-2008-0102756 A     11/2008
(Continued)

OTHER PUBLICATIONS

International Search Report and Written Opinion dated Jul. 25, 2013, issued in corresponding International Application No. PCT/US2013/032561, filed Mar. 15, 2013, 12 pages.

*Primary Examiner* — Pierre E Elisca
(74) *Attorney, Agent, or Firm* — Christensen O'Connor Johnson Kindness PLLC

(57) ABSTRACT

Devices, methods, and systems for monitoring, classifying and encouraging activity through the use of an accelerometer or other sensor in a toy or other accessory (such as a backpack or watch) that records activity are disclosed. The activity is classified, using various motion classification algorithms, to determine the specific types and amount of activities performed and the times and duration for which they were performed. The classified data is used in the rest of the system, which allows users to view activity history, recommendations for how to improve health, and play
(Continued)

games in which the player's game performance is effected by their activity levels. In games and on the website, feedback is also given to users to encourage and reward exercise, while handicapping users that are not active.

18 Claims, 17 Drawing Sheets

(51) Int. Cl.
  *G06Q 50/22* (2018.01)
  *A61B 5/00* (2006.01)
  *A61B 5/11* (2006.01)
(52) U.S. Cl.
  CPC ............ *G06Q 50/10* (2013.01); *G06Q 50/22* (2013.01); *A61B 5/1123* (2013.01); *A61B 5/7264* (2013.01); *A61B 5/744* (2013.01); *A61B 2503/06* (2013.01)

(56) References Cited

U.S. PATENT DOCUMENTS

2010/0167801 A1* 7/2010 Karkanias ............ G06F 19/3418
  463/7
2012/0330109 A1* 12/2012 Tran ..................... A61B 5/0022
  600/301

FOREIGN PATENT DOCUMENTS

WO  2011/020135 A1  2/2011
WO  2011/028386 A1  3/2011

* cited by examiner

|  | Running | Walking | Up Stairs | Down Stairs | Jumping Jacks |
|---|---|---|---|---|---|
| Amount | 711 | 913 | 319 | 343 | 187 |

*Fig. 7.*

| | | Accuracy | |
|---|---|---|---|
| | | 10-Fold Cross Validation | Testing Set |
| Classifiers | J48 | 94.92 | 47.14 |
| | NaiveBayes | 87.93 | 63.50 |
| | OneR | 74.72 | 68.06 |
| | Voting (Average of Probabilities) | 90.87 | 76.43 |
| | Voting (Majority Vote) | 90.55 | 66.92 |

*Fig. 8.*

| Activity | Classified As | | | | |
| --- | --- | --- | --- | --- | --- |
| | Running | Walking | Up Stairs | Down Stairs | Jumping Jacks |
| Running | 51 | 4 | 2 | 2 | 2 |
| Walking | 79 | 13 | 0 | 11 | 2 |
| Up Stairs | 11 | 2 | 9 | 4 | 3 |
| Down Stairs | 3 | 4 | 0 | 20 | 0 |
| Jumping Jacks | 6 | 1 | 1 | 2 | 31 |

*Fig.9.*

| Activity | Classified As | | | | |
| --- | --- | --- | --- | --- | --- |
| | Running | Walking | Up Stairs | Down Stairs | Jumping Jacks |
| Running | 58 | 1 | 0 | 2 | 0 |
| Walking | 2 | 84 | 0 | 17 | 2 |
| Up Stairs | 3 | 1 | 9 | 14 | 2 |
| Down Stairs | 2 | 4 | 1 | 20 | 0 |
| Jumping Jacks | 7 | 1 | 2 | 1 | 30 |

*Fig.10.*

DEVICES, SYSTEMS, AND METHODS FOR MONITORING, CLASSIFYING, AND ENCOURAGING ACTIVITY

CROSS-REFERENCE TO RELATED APPLICATION

This application claims the benefit of U.S. Provisional Application No. 61/614,437, filed Mar. 22, 2012, the entire disclosure of which is hereby incorporated by reference herein for all purposes.

BACKGROUND

Youth obesity is a growing problem in the United States. Currently, nearly one-third of all children may be considered overweight or obese. A contributing factor is the lack of exercise. According to the KFF Institute, children and adolescents aged 2-19 spend on average 7 hours and 38 minutes a day passively consuming media. What is needed are techniques for encouraging physical activity. Though it is often possible to attract children's interest with video games, excessive participation in such sedentary behavior without some incentive to also perform other activities that could constitute exercise can lead to even less exercise.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a system for encouraging physical activity is provided. The system includes a motion sensing device. The motion sensing device is configured to capture motion data representing a user's physical activity. The system also includes a computing device configured to process motion data captured by the motion sensing device to determine activity data. The system also includes a computing device configured to receive the activity data, and to present an interface that includes one or more games for use by the user, wherein one or more attributes of the games are modified based on the received activity data. Similar methods are provided, as are computer-readable media having instructions stored thereon that cause a similar method to be provided.

In some embodiments, a method of encouraging physical activity is provided. Physical activity of a user is monitored using at least one accelerometer to collect motion data. The motion data is analyzed with a computing device to identify one or more activities performed by the user. Attributes of a video game avatar are updated based on the activities performed by the user. A computing device configured to perform a similar method and a computer-readable medium having instructions stored thereon that cause a computing device to perform a similar method are also provided.

DESCRIPTION OF THE DRAWINGS

The foregoing aspects and many of the attendant advantages of embodiments of the present disclosure will become more readily appreciated as the same become better understood by reference to the following detailed description, when taken in conjunction with the accompanying drawings, wherein:

FIG. 7 is a table that shows a number of individual data points per type of activity in an example set of training data according to various aspects of the present disclosure;

FIG. 8 is a table that shows accuracies for various classifiers, 10-fold cross-validation on the training set, and on a testing set, according to various aspects of the present disclosure;

FIG. 9 is a table that presents a confusion matrix for a J48 (C4.5) classifier on the training set;

FIG. 10 is a table that shows a confusion matrix for the Voting Ensemble classifier (using Average of Probabilities) on the training set;

DETAILED DESCRIPTION

System Overview

In some embodiments of the present disclosure, a device with embedded motion sensors, a mobile phone application for alternate data collection, and a website that contains games and rewards are provided. One motivation behind embodiments of the present disclosure is to monitor children's activity and use their activity to influence their ability to play video games. The influence of detected activity in the games may be to reduce or increase the speed or responsiveness of a video game character depending on how often the user has exercised. Additional ways in which embodiments of the present disclosure may provide exercise motivation include providing rewards to users who exercise longer and more frequently.

In some embodiments of the present disclosure, sensing mechanisms that use a minimal number of sensors are embedded within a device such as a toy, such as a toy representing a pet. In order to encourage children to exercise more, a website with avatars of the physical toys is provided. The website offers children the ability to play games using their physical toy's virtual avatar. The avatar in a game may look and perform differently depending on how recently and how much the child has exercised, as detected by the sensing mechanisms within the toy. Thus, a user's desire to play video games and have fun is correlated with increased physical exercise. The games and rewards may require regular physical activity in order for the user to progress and gain more abilities for their pet's virtual avatar.

A user's exercise may be linked to one or more of their physical pets. A physical pet has a corresponding avatar on a website which changes based on the type and quantity of exercise performed. Increased exercise causes the avatar to perform better in games and appear more physically fit. A child who has not exercised frequently will have pet avatars which perform poorly in games and will not allow the child to be able to obtain special rewards for exercising. Embodiments of the present disclosure may be designed to employ a child's desire to play video games to encourage them to increase the amount of physical activity they perform on a regular basis. Additionally, by providing the child with a physical toy rather than just a virtual avatar the child may take the exercise more seriously.

Figure 1A:
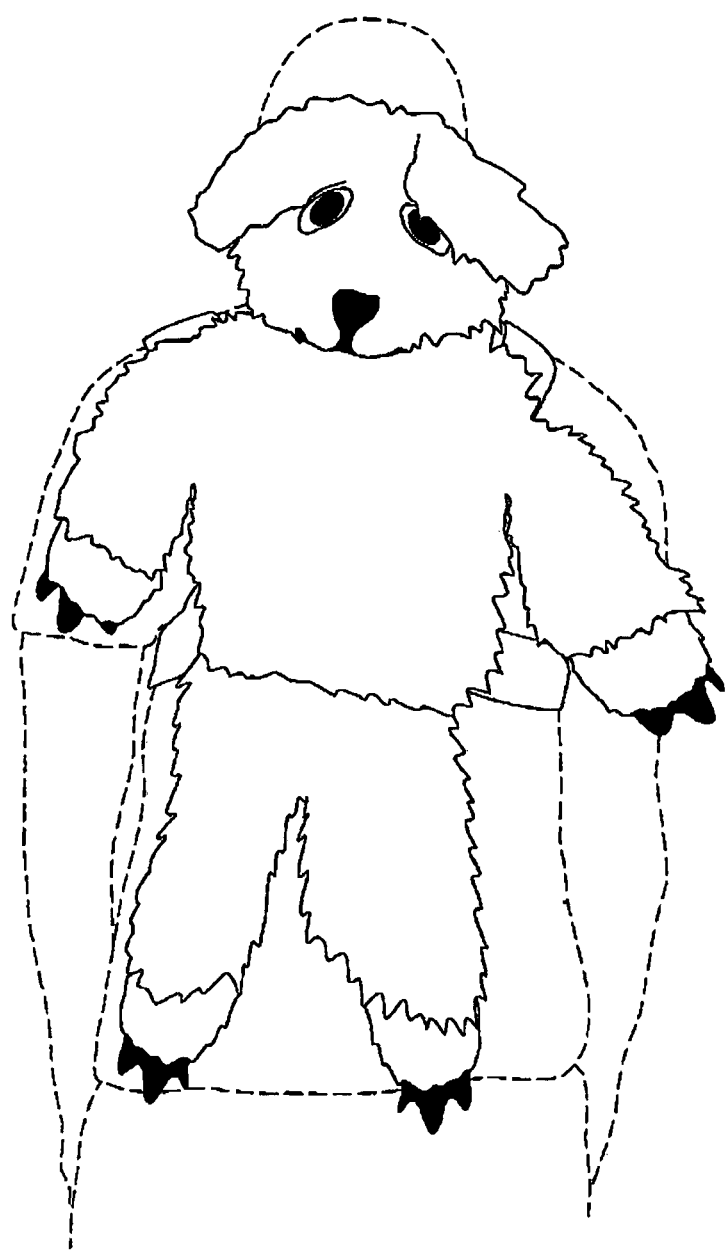
FIGS. 1A-1C depict three exemplary plush toys suitable for use with embodiments of the present disclosure.
Figure 1B:
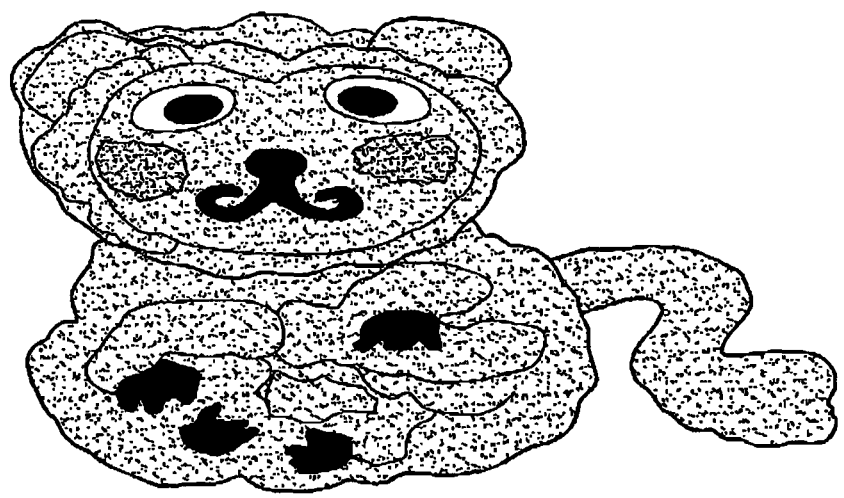
Figure 1C:
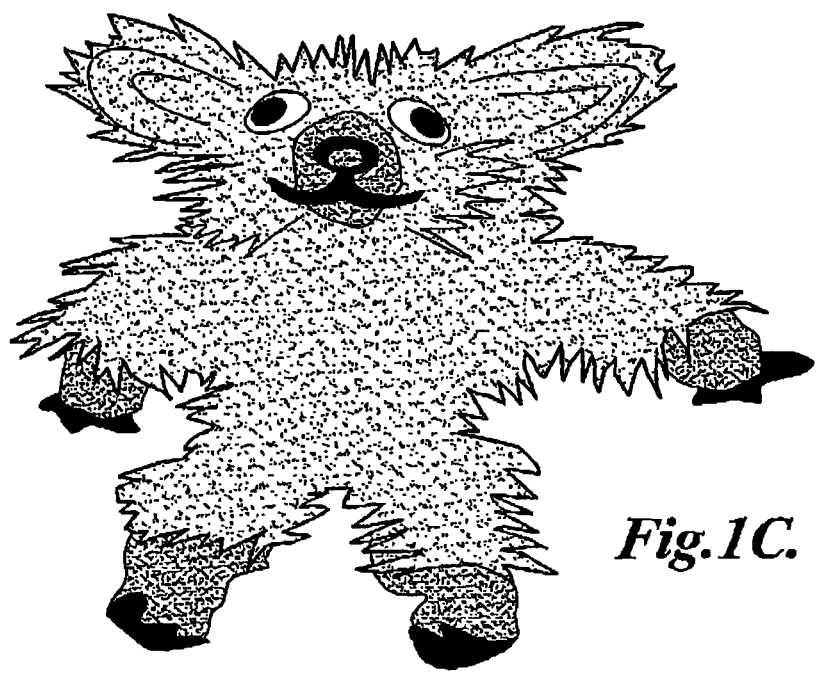

As stated above, the device may be either a toy or accessory, such as a watch or backpack that includes motion sensors configured to record activity levels of a user. FIGS. 1A-1C depict three exemplary plush toys suitable for use with embodiments of the present disclosure. Though not visible in the figure, the plush toys contain accelerometers to monitor activity levels. Since the device will be in motion and used by kids, safety is critical. Accordingly, the illustrated devices were designed without any hard materials, using felt and fabric for the hands, eyes, and nose, instead of any plastics or materials that could potentially cause injury.

In some embodiments, the plush toys may include a flap which allows access to a port of the sensor in order to charge the device and/or transfer data collected by the device. In some embodiments, the device may have wireless capabilities for both data transfer and charging in addition to or instead of the physical port. In some embodiments, the flap may be made from material matching the rest of the device, and may be held in place with a hook-and-loop fastener, a button, or with any other suitable fastening means to allow it to camouflage into the rest of the device while providing easy access to the port for end users, and access to the sensor for maintenance.

Figure 2:
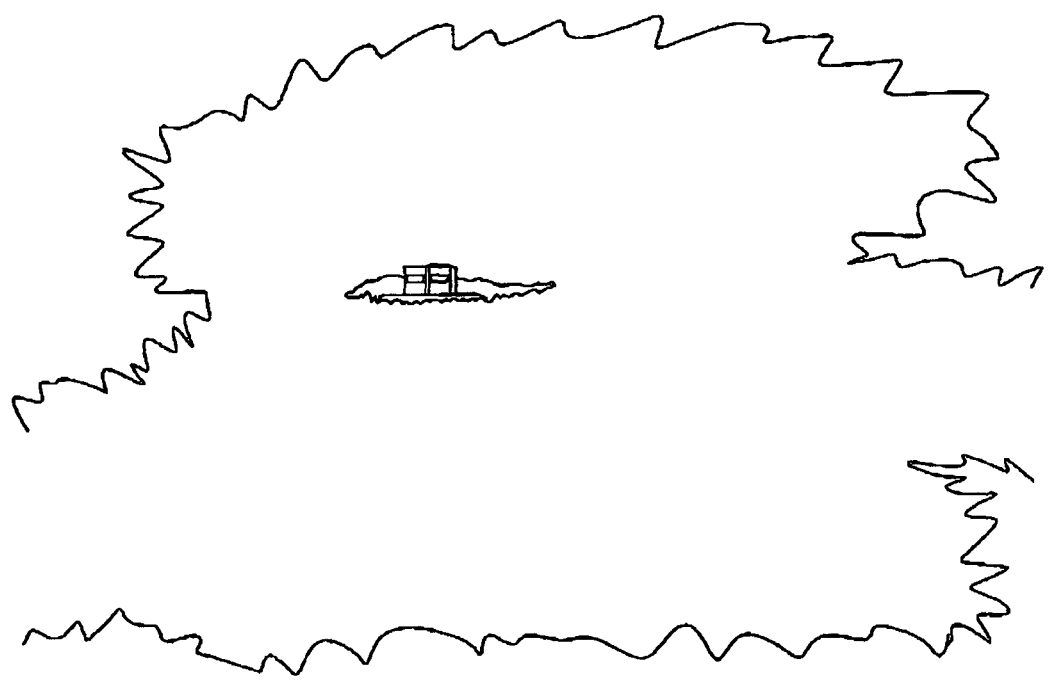
FIG. 2 illustrates a detail of an exemplary flap of a device illustrated in FIG. 1.

FIG. 2 illustrates a detail of an exemplary flap of the device described above. Under the flap, the sensor is encased in foam padding to avoid any hard spots. As shown, by lifting the flap, access may be provided to a data transfer port, such as the illustrated USB port. The foam padding containing the sensor may be removable from a pocket within the device that is disposed under the flap to allow for easy replacement and the ability for the device to accommodate both bigger and smaller sensors. In some embodiments, the sensor may instead be permanently affixed inside the body of the device or toy.

Figure 4:
FIG. 4 is a detail view of a utility pocket according to various aspects of the present disclosure.
Figure 3:
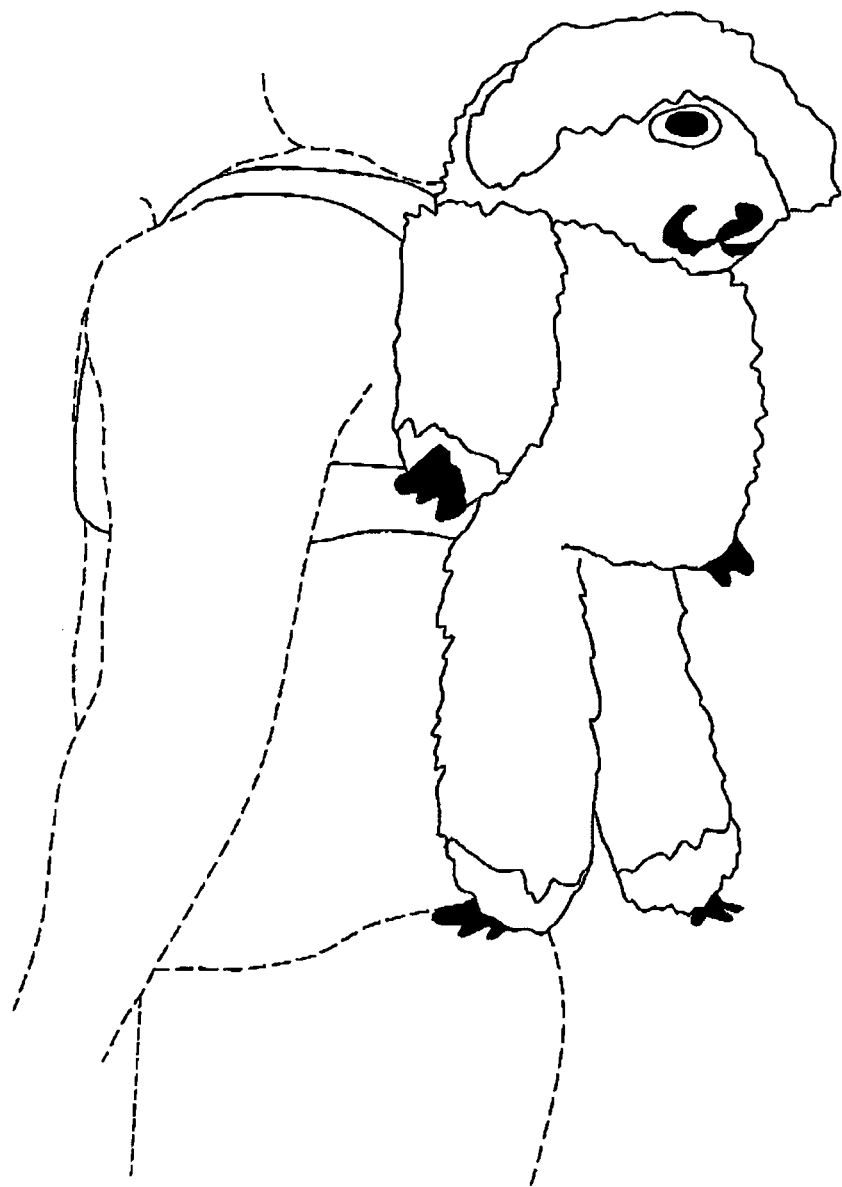
FIG. 3 illustrates an exemplary embodiment of a device that is a plush toy that includes optional backpack straps according to various aspects of the present disclosure.

In some embodiments, the toy or accessory may be designed to be worn to allow for continuous monitoring throughout the day (instead of only while the device is being held or carried by hand. FIG. 3 illustrates an exemplary embodiment of a device that is a plush toy that includes optional backpack straps, thus allowing the device to be worn, and allowing the device to double as a backpack. Further, since the toy or accessory may be carried around at all times, the illustrated plush toy may feature another utility pocket, as illustrated in FIG. 4, to hold things like cellular phone, keys, lunch money, or any other goods. The number and configuration of pockets may vary amongst different devices. The inclusion of utility pockets and/or backpack straps may provide further encouragement and ease of carrying the device during a greater portion of the day, thus allowing more comprehensive monitoring of daily activity. Various other features and functionality may also be added to make the toys and accessories more appealing, such as playfully adjustable tails, a pillow-like toy that encourages the user to carry it around, and/or the like. Likewise, the incorporation of the device into types of wearable accessories other than toys, such as watches, shoes, clothing, wristbands, jewelry, and/or the like, may similarly increase the amount of time that activity is monitored during the day.

Figure 5:
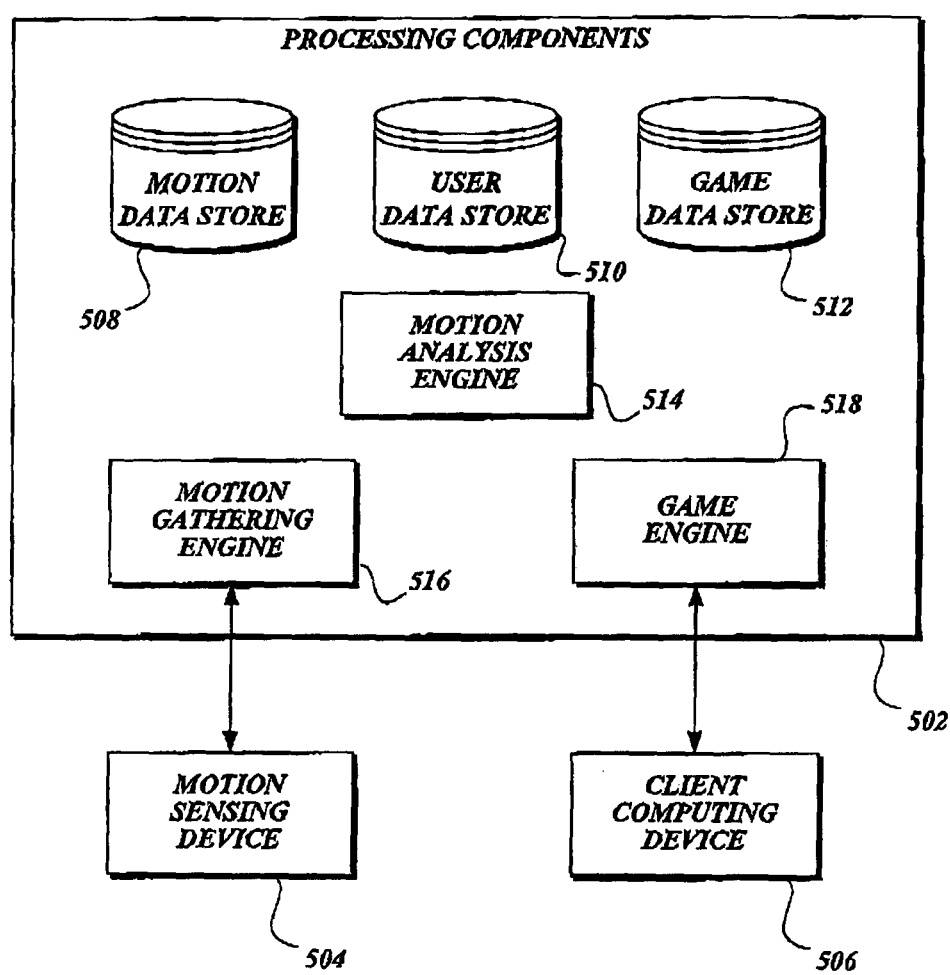
FIG. 5 is a block diagram that illustrates an exemplary embodiment of an activity encouragement system according to various aspects of the present disclosure.
Figure 6A:
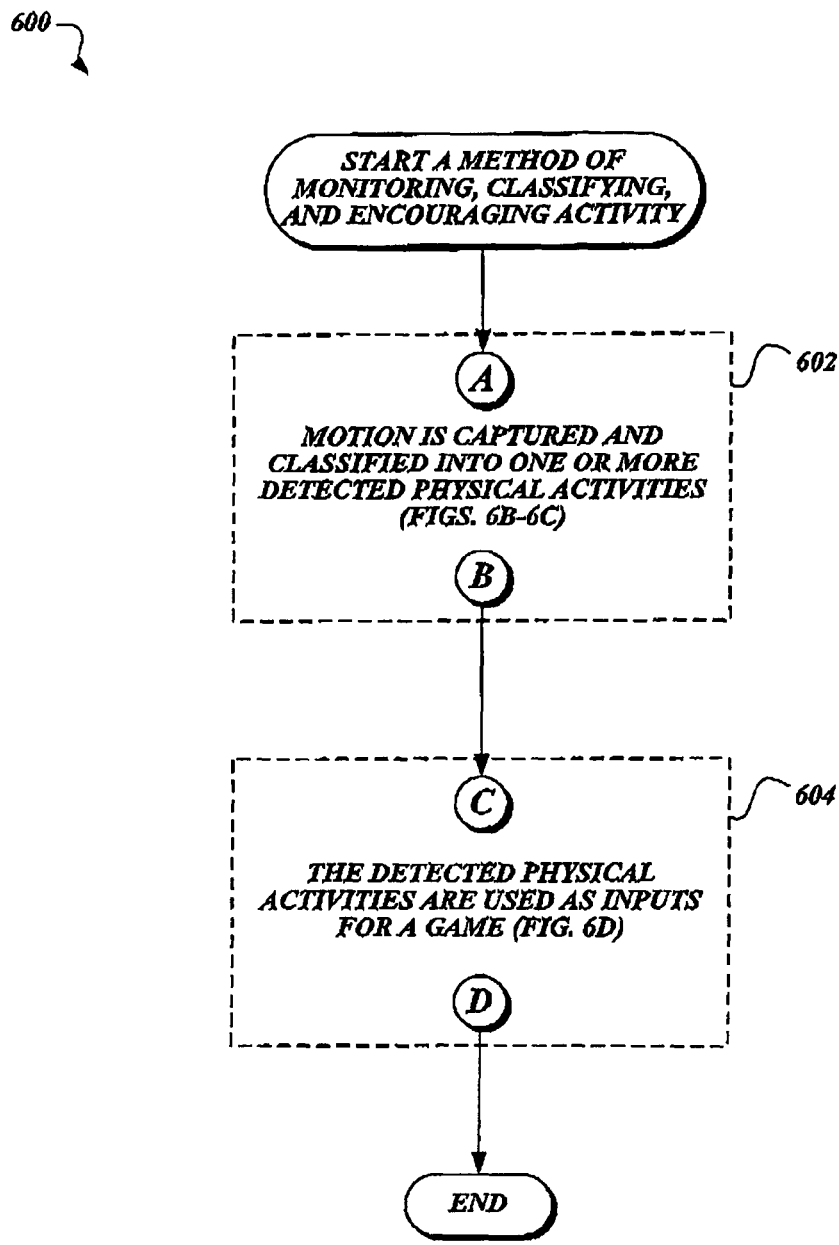
FIGS. 6A-6D are a flowchart that illustrates an exemplary embodiment of a method of monitoring, classifying, and encouraging activity according to various aspects of the present disclosure.
Figure 6B:
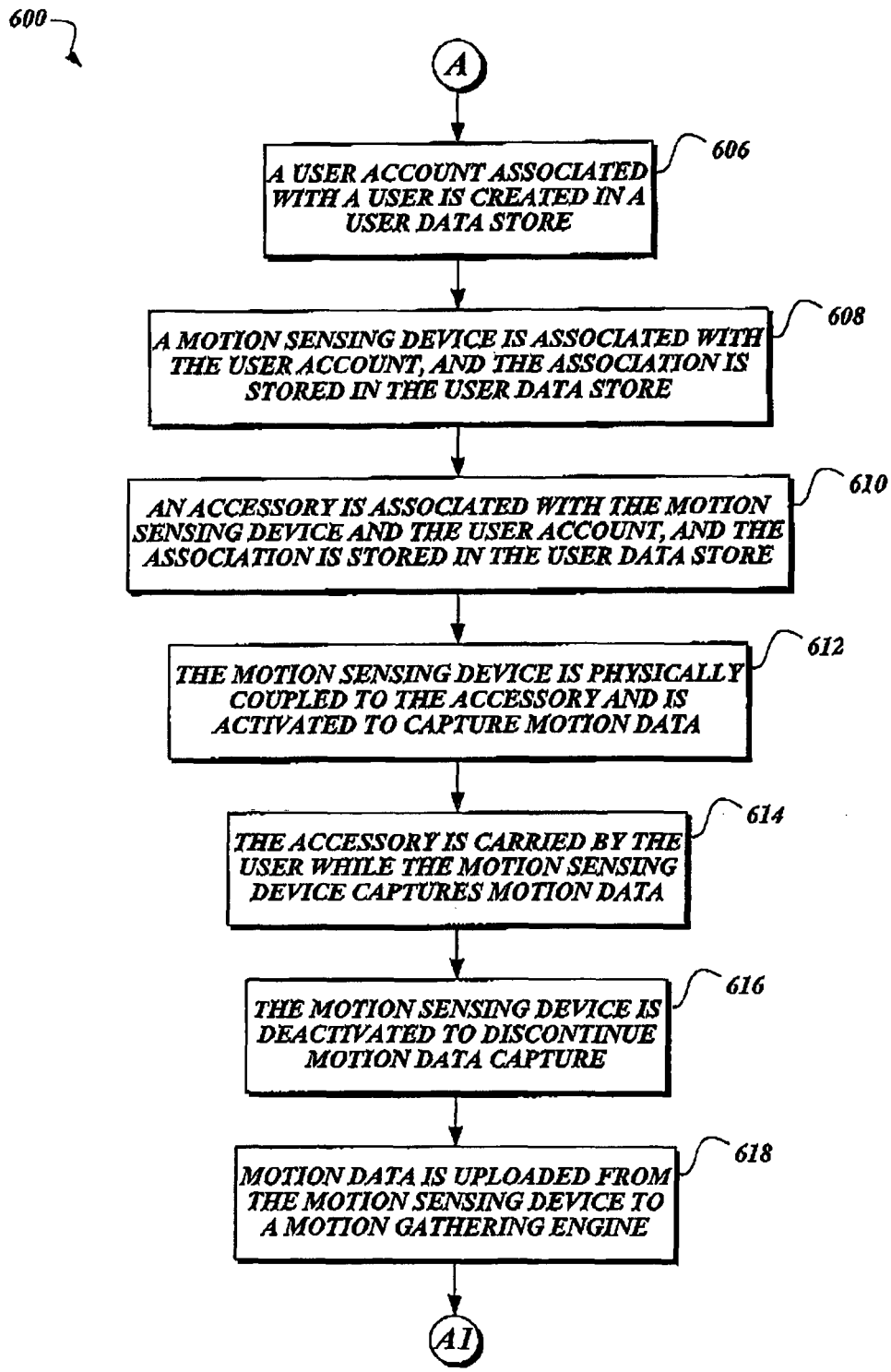
Figure 6C:
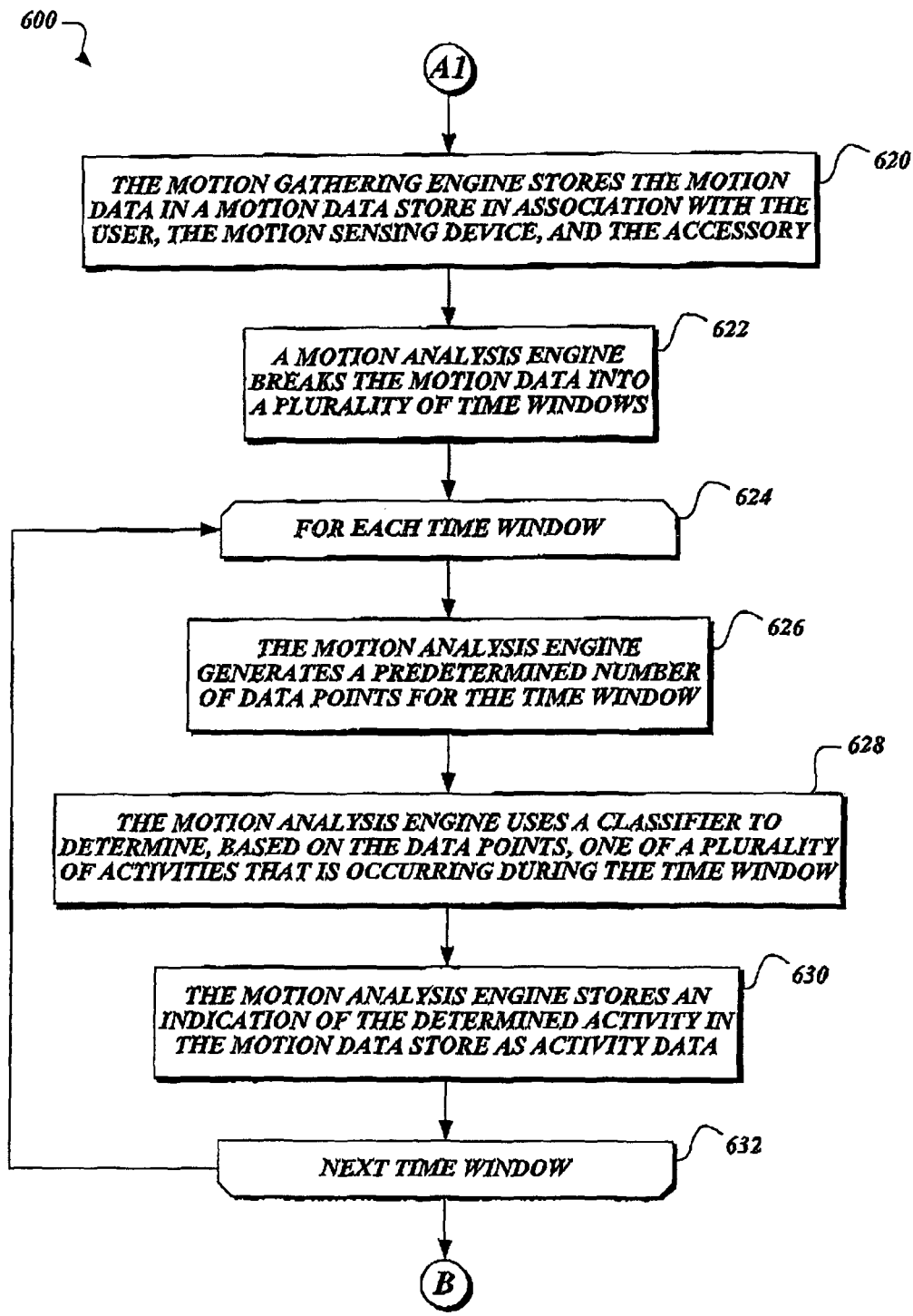
Figure 6D:
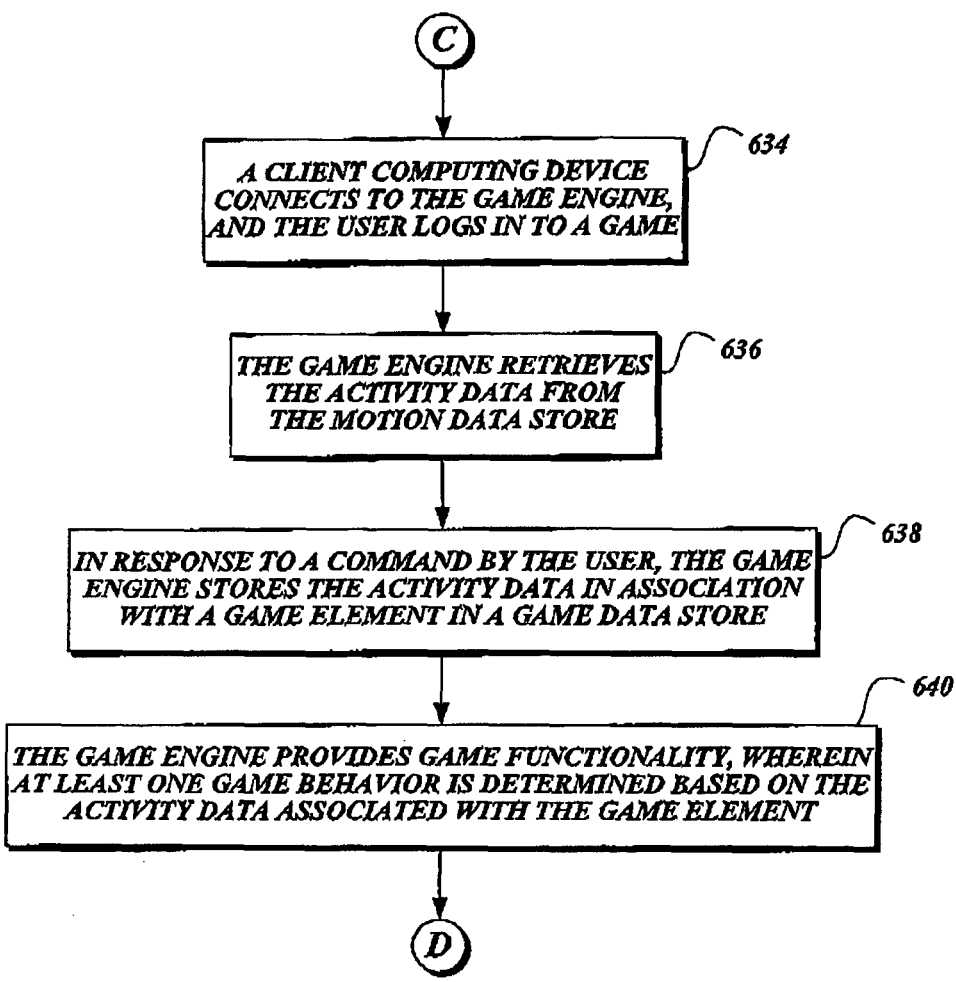

FIG. 5 is a block diagram that illustrates an exemplary embodiment of an activity encouragement system 500 according to various aspects of the present disclosure. The activity encouragement system 500 includes processing components 502, a motion sensing device 504, and a client computing device 506. In some embodiments, the processing components 502 may include one or more server computing devices configured to receive captured motion sensor data, to analyze the motion sensor data to determine one or more represented activities, and to use the activity information in altering game attributes, as described further below. In some embodiments, at least some of the functionality of the processing components 502 may be provided by a server computing device, by a cloud-based service, by a desktop computing device, by a laptop computing device, or by any other suitable computing device capable of performing the described actions.

In some embodiments, the processing components 502 may include a motion gathering engine 516, a motion analysis engine 514, and a game engine 518. In some embodiments, the motion gathering engine 516 is configured to obtain the captured motion sensor data from the motion sensing device 504 upon establishment of a communication path between the motion gathering engine 516 and the motion sensing device 504. In some embodiments, the motion analysis engine 514 is configured to process the captured motion sensor data to detect activities represented by the motion sensor data, and to store the processed data for use in a game. Various ways in which the captured motion sensor data may be processed by the motion analysis engine 514 are discussed further below.

In some embodiments, the game engine 518 may provide an interface associated with one or more games. The game (or games) may use one or more avatars associated with the user, or associated with a user's device or toy. Game mechanics may be affected by the amount of exercise that a user has performed, as recorded by the toy and provided to the processing components 502. In some embodiments, when a user exercises and such activity is captured by the motion sensing device 504 and provided to the processing components 502, an associated avatar in the game is given a certain amount of virtual stamina based on the amount of time they spent doing various activities. When a user plays a game, the avatar may lose a portion of the stamina that it had previously acquired. When an avatar no longer has any stamina its in-game attributes may be modified to cause poorer performance games and/or may appear to be fatter or otherwise less healthy. The motivation for this design is that the user will want their toy to perform better in games and will be motivated to exercise more to increase their in game abilities. In some embodiments, special rewards are given to users who score highly in games or for doing varying amounts of physical activity. In some embodiments, instead of providing a complete game, the game engine 518 may provide an application programming interface (API) that provides access to captured motion data, detected activity data, and/or functionality for manipulating game mechanics based on activity data, such that the API may be used to incorporate functionality of the system 500 for monitoring and encouraging activity into other games or applications developed by third-parties.

In some embodiments, at least portions of the motion gathering engine 516, the motion analysis engine 514, and/or the game engine 518 may be provided by an application executed by a desktop computing device or a laptop computing device to which the motion sensing device 504 is communicatively coupled. In some embodiments, at least portions of the motion gathering engine 516, the motion analysis engine 514, and/or the game engine 518 may be provided by a server computing device or a cloud computing service to which the motion sensing device 504 is communicatively coupled.

In general, an "engine" as described herein refers to logic embodied in hardware or software instructions, which can be written in a programming language, such as C, C++, COBOL, JAVA™, PHP, Perl, HTML, CSS, JavaScript, VB Script, ASPX, Microsoft .NET™ languages such as C#, and/or the like. An engine may be compiled into executable programs or written in interpreted programming languages. Software engines may be callable from other engines or from themselves. Generally, the engines described herein refer to logical modules that can be merged with other engines, or can be divided into sub engines. The engines can be stored in any type of computer readable medium or computer storage device and be stored on and executed by one or more processors of a general purpose computing device, thus creating a special purpose computing device configured to provide the engine and/or the functionality thereof.

In some embodiments, the processing computing device 502 may also include or otherwise have access to a motion data store 508, a user data store 510, and a game data store 512. In some embodiments, the motion data store 508 is configured to store the motion data captured by the motion sensing device 504 and obtained by the motion gathering engine 516. The motion data store 508 may also be configured to store activity data determined by the motion analysis engine 514 based on the motion data. The user data store 510 may be configured to store information associated with users, including but not limited to logins, passwords or PIN information, references to sets of motion data and/or activity data in the motion data store 508, information associating one or more motion sensing devices 504 with users, and/or the like. The game data store 512 may be configured to store information associated with one or more in-game avatars, including but not limited to references to users associated with the avatars, references to motion sensing devices 504 associated with the avatars, game mechanic information associated with the avatars such as a remaining amount of stamina and/or the like, references to sets of activity data from the motion data store 508 including indications of whether the sets of activity data have been applied to the avatar, and/or the like.

As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed packet switched network. However, any other suitable storage technique and/or device capable of quickly and reliably providing the stored data in response to queries may be used, and the computing device may be accessible locally instead of over a network, or may be accessible over some other type of suitable network or provided as a cloud-based service. A data store may also include data stored in an organized manner on a storage medium 1708, as described further below. One of ordinary skill in the art will recognize that separate data stores described herein may be combined into a single data store, and/or a single data store described herein may be separated into multiple data stores, without departing from the scope of the present disclosure.

In some embodiments, the motion sensing device 504 is, as described above, included within a device such as a toy, a wearable accessory, and/or the like, and is carried by the user to monitor the user's activity. In some embodiments, the motion sensing device 504 may include an accelerometer and a computer-readable storage medium configured to temporarily store the detected accelerometer values. Some embodiments may include an off-the-shelf device that requires limited additional configuration to run, and that saves acceleration values at a given frequency to its computer-readable storage medium in an accessible format, such as a comma-separated value (CSV) file and/or the like. One exemplary such device is a Gulf Coast Data Concepts X250-2 Impact Sensor. Such a sensor is capable of measuring acceleration with 14 bits of precision in the ranges of ±250 g or ±28 g in three axes. In some embodiments, such an accelerometer may be set to record acceleration at 64 Hz in the range of ±250 g with no filtering being performed by the device. In other embodiments, other accelerometer data loggers or accelerometer data logger settings may be used without departing from the scope of the present disclosure. As described further herein, the motion sensing device 504 is communicatively coupled to the processing computing device 502 via a wired or wireless data connection, and the motion gathering engine 516 is provided with the values collected by the motion sensing device 504.

In some embodiments, the motion sensing device 504 may be an accelerometer built into a mobile computing device such as a smartphone and/or the like. An application executing on the mobile computing device may be used to collect the information from the accelerometer of the mobile computing device. Despite similarities to the gathered information, due to limitations in accuracy and variations in the frequency of retrieving the accelerometer information recorded by a mobile computing device, in some embodiments a separate classification model (as described below) may be used for analyzing data captured by the mobile computing device to provide accurate results. For example, in some embodiments, the embedded accelerometer in the toy described above may be configured to sample at 64 Hz, but the mobile application may not have the capability to enforce strict time requirements on the measurements received from the built-in accelerometer.

In some embodiments, the client computing device 506 may be any suitable computing device configurable to communicate with the game engine 518 and provide game and/or motion analysis related functionality to users. Some non-limiting examples of suitable computing devices are desktop computing devices, laptop computing devices, tablet computing devices, mobile computing devices such as smartphones, and/or the like. As stated above, some embodiments of the present disclosure include a website, which may be provided by the game engine 518. In some embodiments, when the user uses a client computing device 506 to access the website they are presented with a bright and colorful depiction of a virtual world. The website may offer games and the ability to view uploaded activity history of a virtual pet (or a user associated with a virtual pet). In some embodiments, the website may be built using any suitable web application framework and programming language. In one embodiment, Django 1.2 and Python 2.7.1 may be used, but any other suitable technologies may be used. A DBMS such as PostgreS 15 and/or the like may be used to handle the persistence layer, and the website may be deployed on a traditional server, a cloud computing service, such as an Ubuntu micro instance executing on Amazon Web Services, or any other suitable server platform.

In some embodiments, the website may include a custom web application which manages all of the data and controls the user interfaces presented to the user. The web application supports both parents and children interacting with the website in different manners. Children are presented with games and avatars of their physical toys. Parents are able to log in to check up on their children and determine how much and how frequently they have been exercising. Additionally, parents are able to determine how many games their children have played over the last day or week.

In some embodiments, the website also provides an application programming interface (API) in order to enable easy communication between outside applications and the main website and database. In some embodiments, the application programming interface provides a RESTful interface that is easy to understand and use in other applications. Authentication techniques such as OAuth may be used to authenticate applications to the API in order to store a secure token, rather than storing plaintext username and passwords to authenticate the user, though any suitable authentication scheme may be used. The tokens may be assigned on a per user, per application basis, so that users can easily revoke permissions from a specific application. One use for the API is to allow the desktop application to have easy access to data stored in the website database as well as to sync the amount of exercise that the user has performed. The API may also be used to integrate social networking into the system, such as by sharing activity data or game information with a social networking platform such as Facebook and/or the like.

Methods of Mounting and Encouraging Activity

FIGS. 6A-6D are a flowchart that illustrates an exemplary embodiment of a method of monitoring, classifying, and encouraging activity according to various aspects of the present disclosure. From a start block, the method 600 proceeds to a set of method steps 602 defined between a start terminal ("terminal A") and an exit terminal ("terminal B"). The set of method steps 602 includes actions wherein motion is captured and classified into one or more detected physical activities.

From terminal A (FIG. 6B), the method 600 proceeds to block 606, where a user account associated with a user is created in a user data store 510. The user account may include a user name, a real name, a password or PIN, and/or any other information to be associated with the user. At block 608, a motion sensing device 504 is associated with the user account, and the association is stored in the user data store 510. At block 610, an accessory is associated with the motion sensing device 504 and the user account, and the association is stored in the user data store 510. In some embodiments, the accessory and the motion sensing device 504 may be permanently coupled or otherwise integrated with each other, in which case only one association between the accessory-device combination and the user account would be created (or separate associations between the integrated accessory and the user and between the integrated motion sensing device 504 and the user could be created at once). In some embodiments, the motion sensing device 504 may be swappable between different accessories, such as an embodiment in which a single motion sensing device 504 may be moved from one toy to another. In such embodiments, separate associations between the motion sensing device 504 and the user and between the accessory and the user may be useful.

The method 600 then proceeds to block 612, where the motion sensing device 504 is physically coupled to the accessory and is activated to capture motion data. At block 614, the accessory is carried by the user while the motion sensing device 504 captures motion data, and at block 616, the motion sensing device 504 is deactivated to discontinue motion data capture. In some embodiments, the motion sensing device 504 may temporarily store the captured motion data in a computer-readable medium incorporated within, coupled to, or otherwise locally accessible by the motion sensing device 504. In some embodiments, the motion sensing device 504 may wirelessly transmit the captured motion data to a storage device while the motion data is being captured. At block 618, the motion data is uploaded from the motion sensing device 504 to a motion gathering engine 516. As discussed above, the motion data may be uploaded to the motion gathering engine 516 using any suitable technique, such as by establishing a USB data connection between the motion sensing device 504 and the motion gathering engine 516, establishing a wireless data connection such as WiFi, Bluetooth, near field communication (NFC), and/or the like between the motion sensing device 504 and the motion gathering engine 516, or any other suitable technique. The method 600 then proceeds to a continuation terminal ("terminal A1").

From terminal A1 (FIG. 6C), the method 600 proceeds to block 620, where the motion gathering engine 516 stores the motion data in a motion data store 508 in association with the user, the motion sensing device 504, and the accessory. In some embodiments, if the user is associated with more than one accessory, an interface may be provided to allow the user to indicate an accessory with which the motion data should be associated. In some embodiments, a previously stored association between the motion sensing device 504 and the accessory may be used to indicate the accessory to associate with the motion data. One of ordinary skill in the art will understand that, in some embodiments, the data gathering steps described in blocks 612-618 may be performed before the user account creation steps described in blocks 606-610, but in most embodiments, steps between block 606 and block 618 are performed before the steps described in block 620.

Once the motion data is obtained, the processing components 502 may proceed to analyze the motion data to determine activities that were conducted while monitoring was enabled. At block 622, a motion analysis engine 514 breaks the motion data into a plurality of time windows. Each time window represents a segment of time for which an activity will be determined. In one embodiment, a time window of two seconds may be used, although other fixed time width intervals may be used. In some embodiments, adjacent intervals may overlap. For example, in one embodiment, the first three two-second intervals may correspond to the data collected in 0-2 seconds, 1-3 seconds, and 2-4 seconds, respectively. In an embodiment wherein the motion sensing device 504 collects data at a rate of 64 Hz, this would lead to 128 readings being associated with each time window.

The method 600 then proceeds to a for loop defined between a for loop start block 624 and a for loop end block 632. The steps in the for loop are repeated for each time window.

From the for loop start block 624, the method 600 proceeds to block 626, where the motion analysis engine 514 generates a predetermined number of data points for the time window. Each time window may include a plurality of readings. For example, in an embodiment wherein the motion sensing device 504 captures motion data at a rate of 64 Hz, each two-second window may include 128 readings. Each reading may be processed to generate features represented by the motion data. For example, in one embodiment, the accelerometer data may be processed to generate twelve features for each interval, including the energy of the X, Y, and Z axes, the correlation between the X&Y, Y&Z, and X&Z axes, the standard deviation of the measurements in the X, Y, and Z axes, and the mean values of the X, Y, and Z axes. In other embodiments, other features may be generated. The twelve features generated for each of the 128 readings may be generated to make up the predetermined number of data points.

At block 628, the motion analysis engine 514 uses a classifier to determine, based on the data points, one of a plurality of activities that is occurring during the time window. The classifier used may be determined based at least in part on an identification or attribute of the user, an identification of the motion sensing device 504, and/or on any other appropriate attribute of the motion data. Further description of generating one or more classifiers is provided below. Once an activity is determined for the time window, the method 600 proceeds to block 630, where the motion analysis engine 514 stores an indication of the determined activity for the time window in the motion data store 508 as activity data.

Techniques such as the above may be useful for recognizing any type of activity that may be detected using X, Y, and Z motion data. Some example activities that may be recognized include, but are not limited to, walking, running, climbing up stairs, climbing down stairs, jumping jacks, jumping up, long jumping forward, push-ups, swinging a tennis racket, pull-ups, jogging, sleeping (or determining sleep quality), spinning in space, cartwheels, and being carried by a vehicle. In some embodiments, the motion data may be analyzed as pedometer data, and the activity data may include a number of detected steps. In some embodiments, motion data may be classified to determine previously unknown classes of activity through unsupervised clustering techniques such as k-min and community finding. In some embodiments, motion data may be classified using semi-supervised learning techniques which utilize at least some labeled activities of the types listed above.

The method 600 then proceeds to the for loop end block 632. If there are further time windows to be processed, the method 600 returns to for loop start block 624. Otherwise, the method 600 proceeds to terminal B.

From terminal B (FIG. 6A), the method 600 proceeds to a set of method steps 604 defined between a start terminal ("terminal C") and an exit terminal ("terminal D"). The set of method steps 604 includes actions wherein the detected physical activities are used as inputs for a game.

From terminal C (FIG. 6D), the method 600 proceeds to block 634, where a client computing device 506 connects to the game engine 518, and the user logs in to a game. At block 636, the game engine 518 retrieves the activity data from the motion data store 508. In some embodiments, the game engine 518 may analyze the activity data to determine effects of the activity data on a game mechanic. In some embodiments, performance of an avatar (such as speed, jumping ability, and/or the like) may be determined by a stamina rating. The game engine 518 may analyze the activity data, and may increase the stamina rating of the avatar based on the analysis. For example, the game engine 518 may determine a total amount of time spent running and climbing up stairs, and for each minute, the game engine 518 may add a point to the stamina rating of the avatar. As another example, the game engine 518 may total up all activity time spent performing non-sedentary activities, and if the total time is greater than a threshold, various game elements may be unlocked for use. In some embodiments, the effects granted by the game engine 518 may diminish, such that more activity would have to be reported in order to restore the increased avatar powers.

Next, at block 638, in response to a command by the user, the game engine 518 stores the activity data in association with a game element in a game data store 512. In some embodiments, the command may be a simple confirmation to associate the selected activity data with a game element, while in other embodiments, the command may include a selection of one or more game elements to be affected. For example, activity points may be spent on a chosen feature to be unlocked, while other features remain locked. The game engine 518 may record that the selected activity data has been applied to a game element, so that the selected activity data is not applied more than once.

At block 640, the game engine 518 provides game functionality, wherein at least one game behavior is determined based on the activity data associated with the game element. In some embodiments, the game functionality, including an interface, may be generated by the game engine 518 for presentation on the client computing device 506.

In some embodiments, the interface and game mechanics may be generated on the client computing device 506, while individual features of the game mechanics may be enabled or disabled via an API provided by the game engine 518.

In some embodiments, the game engine 518 may use the activity data to cause actions outside of the video game environment as well. For example, some physical toys may include features that allow them to get skinnier or fatter, or to otherwise look more or less healthy or happy, in response to instructions generated by the game engine 518 in response to the activity data.

The method 600 then proceeds to terminal D, and then to an end block (FIG. 6A), where the method 600 terminates.

Motion Classification and Classifier Testing

The technique used by various embodiments of the present disclosure for motion classification is to pose motion classification as a machine learning problem. During a training phase, the user is requested to perform only one activity for a period of time and all of the data collected during that time period is labeled as being that activity. This process proceeds for each activity that the system is configured to recognize. Once the motion analysis engine 514 has obtained labeled training data for each activity from the user that it wishes to recognize, it proceeds to generate a classifier using machine learning software, such as the WEKA Java API and/or the like. In some embodiments, the classifier may be implemented using any other suitable technique, such as using a graph theoretic technique or a clustering technique.

In one embodiment, the classifier may be a single J48 (C4.5) decision tree classifier, however, in other embodiments, a classifier voting scheme may be used for higher overall accuracy. The WEKA classifier is then serialized, converted to base64 character encoding, and stored by the motion analysis engine 514. In some embodiments, the classifier may be stored in association with a user account in the user data store 510. This allows the user to access their classifier from a new toy or other device easily and without having to retrain.

Requiring too much training data may ask the user to perform the same action repeatedly for too long and risks making the calibration stage too burdensome. Requiring too little training data may cause the classification model to be insufficient and inaccurate. Through experimentation of using the device on a single individual, it was found that performing an activity for 3-5 minutes is sufficient to produce a classifier with reasonable accuracy.

Though the above describes training personal classifiers, generic classifiers may be stored by the motion analysis engine 514 to attempt to analyze motion data for which a personal classifier has not been trained. In some embodiments, if personal classifiers are used, the motion sensing device 504 may be configured to detect a pattern of motion that is indicative of the person who trained the classifier, and may only collect motion data upon detecting the indicative pattern of motion to prevent mismatches between collected data and utilized classifiers.

Testing was conducted on a single individual using approximately 3-5 minutes of training instances per activity. FIG. 7 is a table that shows the number of individual data points per type of activity in this example. FIG. 8 is a table that shows accuracies for various classifiers, 10-fold cross-validation on the training set, and on a testing set. As shown, the 10-fold cross validation on the training data set had an accuracy of 93% when using a J48 (C4.5) decision tree. FIG. 9 is a table that presents a confusion matrix for the J48 (C4.5) classifier on a training set. The confusion matrix in FIG. 9 shows some activities such as Walking/Running showing higher incidences of misclassification. 10-Fold cross validation doesn't tell the whole story as the results below will show. The 10-fold cross-validation shows how accurately the classifier performs on the training data set. High 10-fold cross validation accuracy may also indicate that the classifier is overfitted to the data, which may make it perform poorly on the testing sets. As we can see in FIG. 8 the Voting ensemble has a lower 10-fold cross validation accuracy but performs more accurately on the testing data set.

These tables show the results of one training/testing session. The training set data was recorded several days prior to recording the testing data set. Involving more individuals in the training/testing process may provide increased confidence in the results in order to make more general conclusions.

The J48 decision tree has the best 10-fold cross validation on the training set, however it performs the worse on the testing set. The most likely scenario is that the decision tree is overfit to the training data, a common problem width decision trees.

The classification method that obtained the best results on the testing sets was the Voting ensemble consisting of a J48, OneR, and NaiveBayes classifiers. Using the Average of Probabilities rather than majority voting in the ensemble was found to yield better accuracy over several testing data sets. In Majority Voting each classifier determines the class which has the highest probability and the one with the most votes is chosen as the result for the ensemble. In the case of ties, the voting ensemble uses a random number generator to determine the class. In combining the classifiers using the Average of Probabilities, the probability that each classifier assigns to each class as the likelihood that the instance belongs to that class is averaged across all classifiers and the class with the highest average probability is selected as the result of the ensemble.

FIG. 10 is a table that shows a confusion matrix for the Voting Ensemble classifier (using Average of Probabilities) on a training set. The confusion matrix in FIG. 10 shows fewer misclassified instances for the ensemble classifier than the J48 classifier alone. Although, the ensemble classifier performs with less misclassification than the J48 classifier both seem to struggle on classifying the "Up Stairs" activity. There are several possible reasons for why this activity is misclassified. One possibly reason is that the testing set for the "Up Stairs" activity actually contains other motions besides just climbing up stairs. This is possible since most stair cases have flat surfaces separating different flights of stairs. Another possible explanation is that the act of walking up stairs results in very similar accelerations when compared to other activities. Further testing across more individuals could eliminate any doubts as to the cause of this misclassification. Using a voting ensemble of trained classifiers results in 70-80% accuracy in recognizing the trained motions.

Exemplary Interfaces

FIGS. 11-16 illustrate various exemplary interfaces associated with applications and games provided by the activity encouragement system 500, according to various aspects of the present disclosure.

Figure 11:
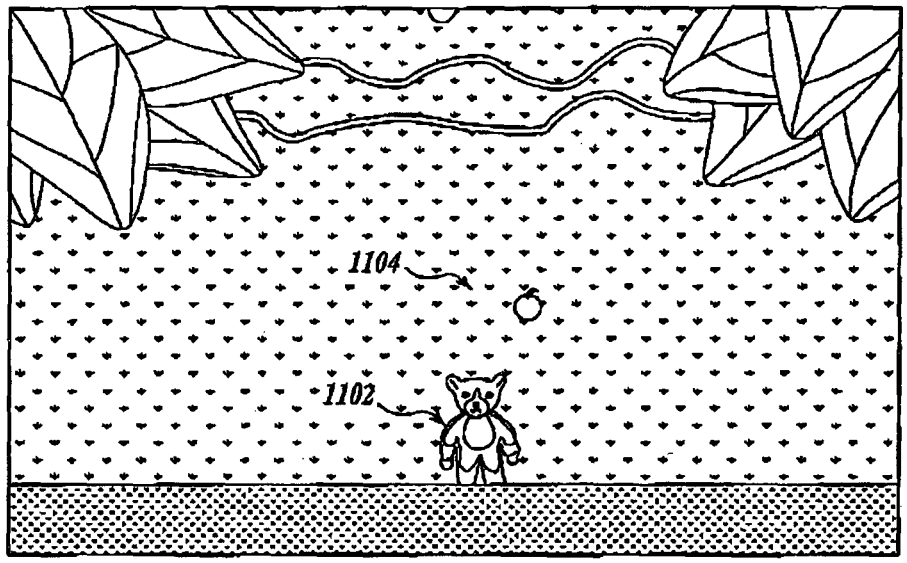
FIGS. 11-16 illustrate various exemplary interfaces associated with applications and games provided by the activity encouragement system according to various aspects of the present disclosure.
Figure 12:
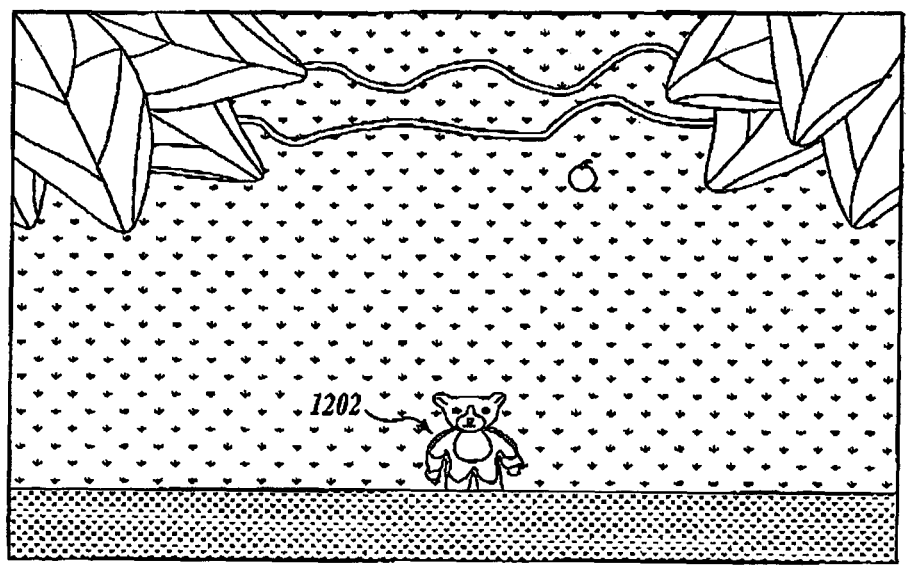

FIGS. 11 and 12 are two illustrations of a game associated with various aspects of the present disclosure. In FIG. 11, an avatar 1102 is depicted. An object of the game is to move the avatar left and right on the interface to avoid apples 1104 falling from the top of the screen. The avatar 1102 is comparatively thin, and so may be able to move quickly and more easily dodge the apples 1104. This avatar 1102 may be associated with a user that recently uploaded activity data that met thresholds to make the avatar 1102 thin, or that caused a stamina level of the avatar 1102 to be raised to a point where the avatar 1102 appears thin due to the stamina level.

FIG. 12 illustrates an avatar 1202 that is comparatively fat. The avatar 1102 above may transition to the fatter avatar 1202 if stamina has been spent without uploading more activity data. The fatter avatar 1202 may not move as quickly, and so will have a harder time dodging the falling apples.

Figure 13:
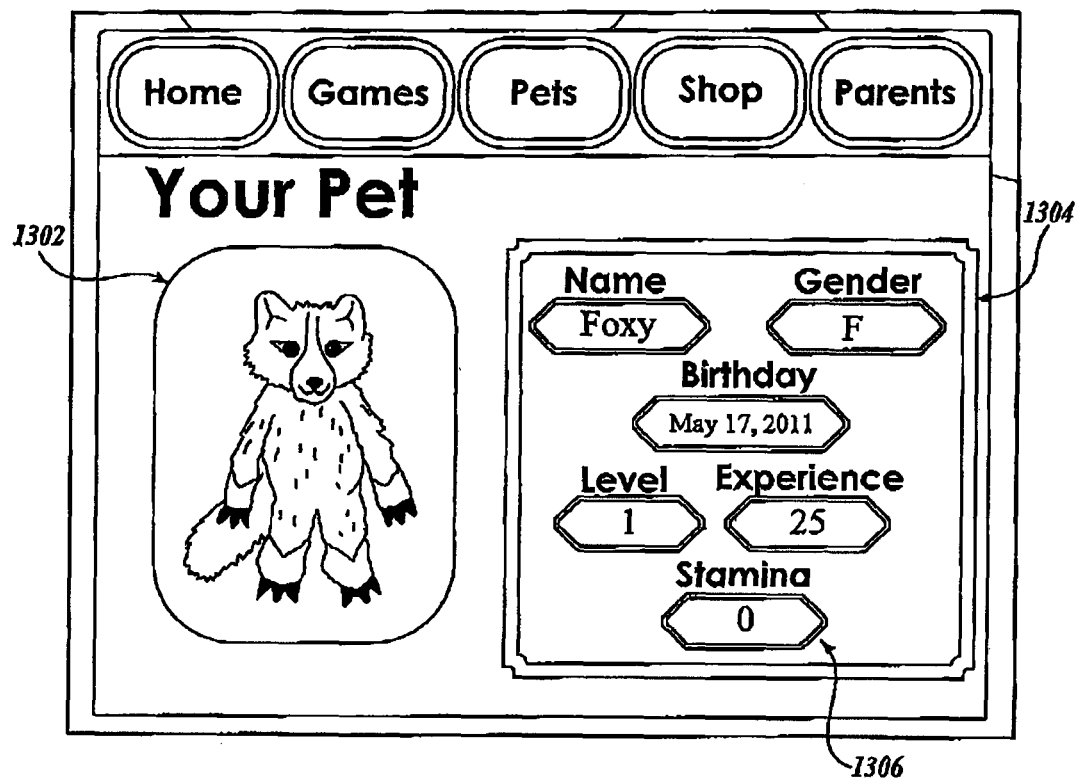

FIG. 13 illustrates an avatar detail interface associated with various aspects of the present disclosure. An avatar picture 1302 is displayed, which may resemble the appearance of the toy or accessory associated with the user. An avatar attribute area 1304 may display one or more attributes of the avatar, including a stamina rating 1306. The stamina rating 1306 may be increased as discussed above by uploading activity data, which will allow the avatar to gain levels and experience faster.

Figure 14:

FIG. 14 illustrates an achievement interface associated with various aspects of the present disclosure. Achievements may be awarded for various in-game acts, or for acts detected in activity data (such as running for a minimum amount of time, and/or the like). When an achievement is reached, a badge 1402 may be presented in the achievement interface to further encourage obtaining achievements.

Figure 15:
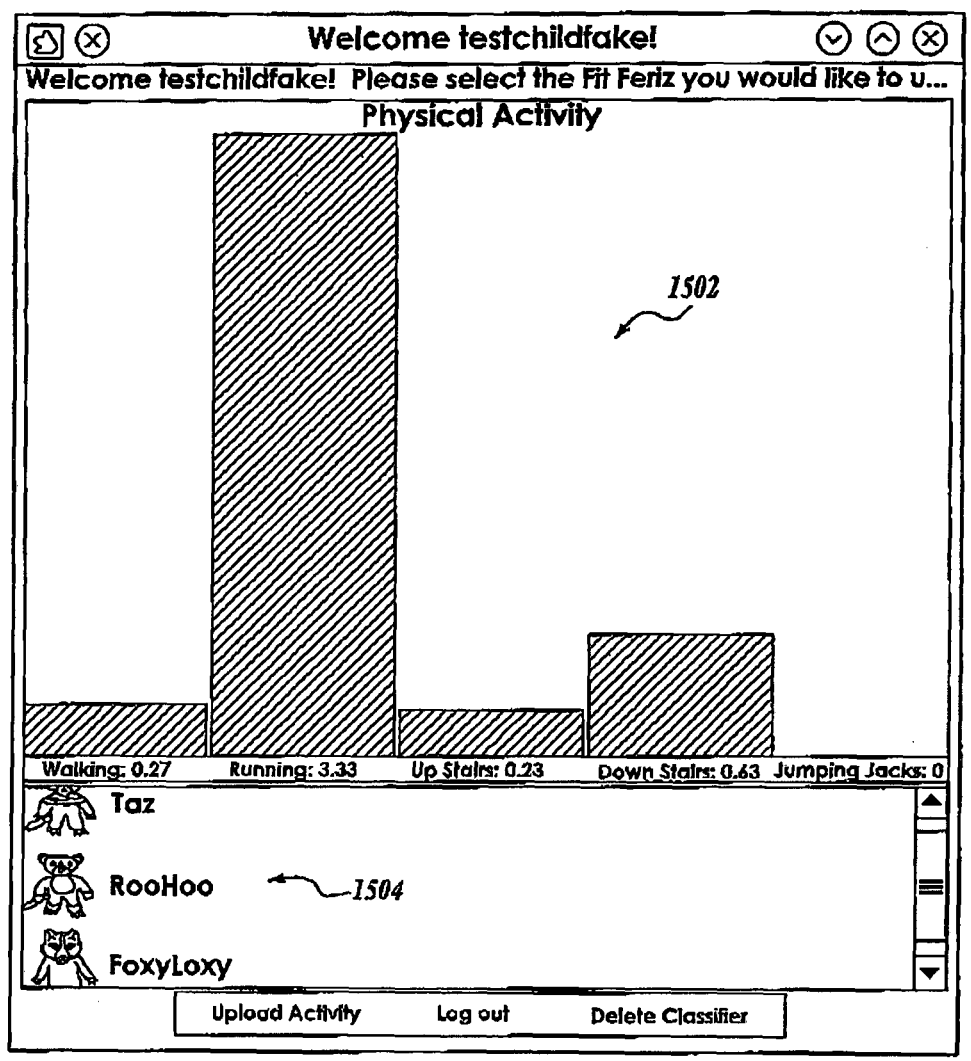

FIG. 15 illustrates an activity upload interface according to various aspects of the present disclosure. Such an interface may be presented by the game engine 518 or motion gathering engine 516 after the analysis of the motion data has been performed. A bar chart 1502 indicates how much of each activity was detected in the motion data, and an avatar select box 1504 allows the user to select which avatar the activity information should be associated with to improve its in-game performance.

Figure 16:
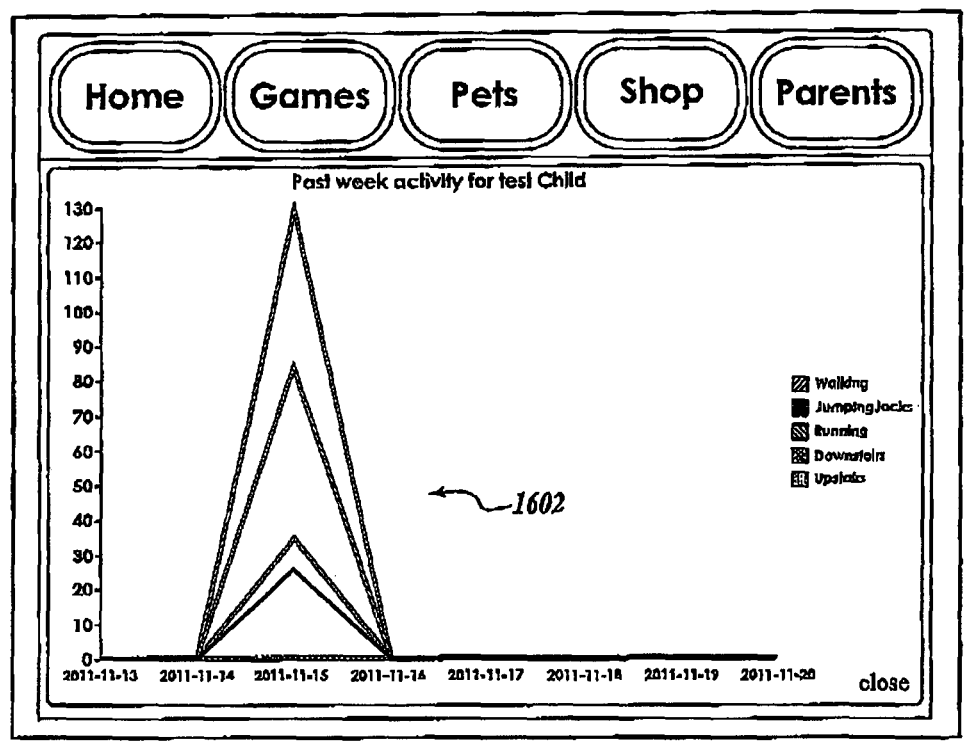

FIG. 16 illustrates one aspect of a parental interface according to various aspects of the present disclosure. Once the motion data has been uploaded and classified into activity information, an activity graph 1602 may be presented to a user such as a parent of a child user, so that the parent may monitor the types and amounts of physical activity that the child is performing.

Exemplary Computing Device

Figure 17:
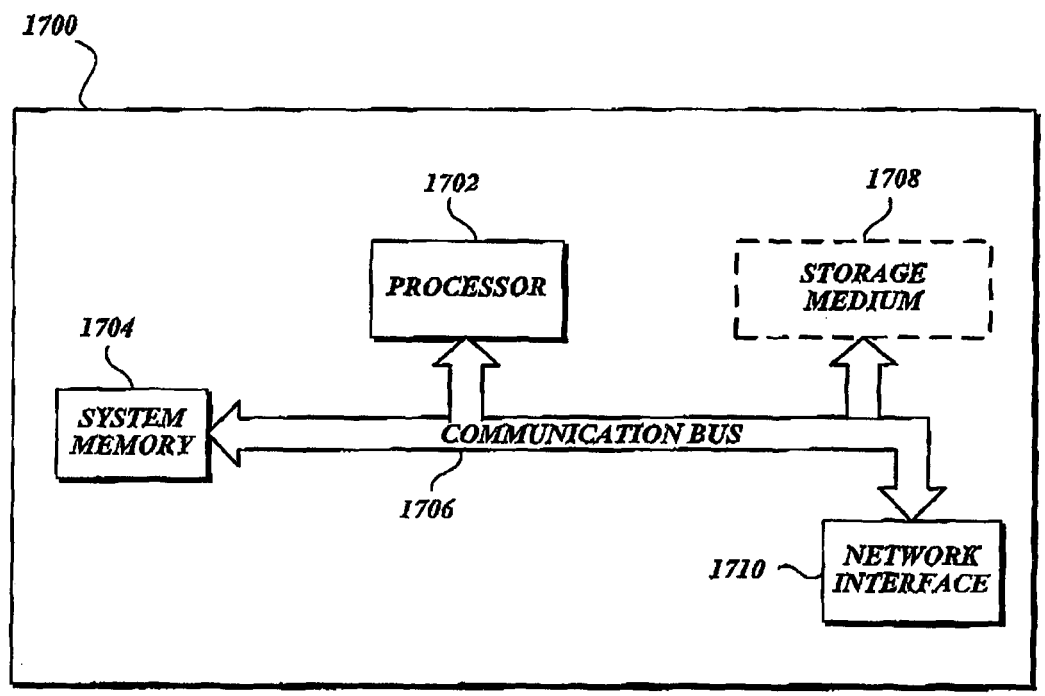
FIG. 17 illustrates aspects of an exemplary computing device appropriate for use with embodiments of the present disclosure.

FIG. 17 illustrates aspects of an exemplary computing device 1700 appropriate for use with embodiments of the present disclosure. While FIG. 17 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 1700 may be any one of any number of currently available or yet to be developed devices.

In its most basic configuration, the computing device 1700 includes at least one processor 1702 and a system memory 1704 connected by a communication bus 1706. Depending on the exact configuration and type of device, the system memory 1704 may be volatile or nonvolatile memory, such as read only memory ("ROM"), random access memory ("RAM"), EEPROM, flash memory, or similar memory technology. Those of ordinary skill in the art and others will recognize that system memory 1704 typically stores data and/or program modules that are immediately accessible to and/or currently being operated on by the processor 1702. In this regard, the processor 1702 may serve as a computational center of the computing device 1700 by supporting the execution of instructions.

As further illustrated in FIG. 17, the computing device 1700 may include a network interface 1710 comprising one or more components for communicating with other devices over a network. Embodiments of the present disclosure may access basic services that utilize the network interface 1710 to perform communications using common network protocols. The network interface 1710 may also include a wireless network interface configured to communicate via one or more wireless communication protocols, such as WiFi, 2G, 3G, LTE, WiMAX, Bluetooth, and/or the like.

In the exemplary embodiment depicted in FIG. 17, the computing device 1700 also includes a storage medium 1708. However, services may be accessed using a computing device that does not include means for persisting data to a local storage medium. Therefore, the storage medium 1708 depicted in FIG. 17 is represented with a dashed line to indicate that the storage medium 1708 is optional. In any event, the storage medium 1708 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 1704 and storage medium 1708 depicted in FIG. 17 are merely examples of computer-readable media.

Suitable implementations of computing devices that include a processor 1702, system memory 1704, communication bus 1706, storage medium 1708, and network interface 1710 are known and commercially available. For ease of illustration and because it is not important for an understanding of the claimed subject matter, FIG. 17 does not show some of the typical components of many computing devices. In this regard, the computing device 1700 may include input devices, such as a keyboard, keypad, mouse, microphone, touch input device, touch screen, tablet, and/or the like. Such input devices may be coupled to the computing device 1700 by wired or wireless connections including RF, infrared, serial, parallel, Bluetooth, USB, or other suitable connections protocols using wireless or physical connections. Similarly, the computing device 1700 may also include output devices such as a display, speakers, printer, etc. Since these devices are well known in the art, they are not illustrated or described further herein.

As will be appreciated by one skilled in the art, the specific routines described above in the flowcharts may represent one or more of any number of processing strategies such as event-driven, interrupt-driven, multi-tasking, multi-threading, and the like. As such, various acts or functions illustrated may be performed in the sequence illustrated, in parallel, or in some cases omitted. Likewise, unless explicitly stated, the order of processing is not necessarily required to achieve the features and advantages, but is provided for ease of illustration and description. Although not explicitly illustrated, one or more of the illustrated acts or functions may be repeatedly performed depending on the particular strategy being used. Further, these FIGURES may graphically represent code to be programmed into a computer readable storage medium associated with a computing device.

Various principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the disclosed subject matter.

Though headings may be used above to denote sections of the detailed description, these headings are provided for ease of discussion only. The headings do not denote separate embodiments, and in some embodiments, discussion from separate headings may be combined into a single embodiment of the present disclosure.

The embodiments of the invention in which an exclusive property or privilege is claimed are defined as follows:

1. A system for encouraging physical activity, comprising:
 a motion sensing device configured to capture motion data representing a user's physical activity;
 a computing device configured to process motion data captured by the motion sensing device to determine activity data, wherein processing motion data captured by the motion sensing device includes classifying motion data captured by the motion sensing device as one or more of a plurality of types of physical activity, and wherein classifying motion data includes at least one of:
  classifying motion data using a voting ensemble; and
  using an unsupervised clustering technique or a semi-supervised clustering technique to classify motion data representing previously unknown types of physical activities; and a computing device configured to:
  receive the activity data; and
  present an interface that includes one or more games for use by the user, wherein one or more attributes of the games are modified based on the received activity data.

2. The system of claim 1, further comprising an accessory, wherein the motion sensing device is coupled to the accessory.

3. The system of claim 2, wherein the accessory is selected from a group consisting of a toy, a watch, a shoe, an article of clothing, a wristband, an item of jewelry, a smartphone, and a mobile computing device.

4. The system of claim 3, wherein the toy includes at least one removable strap for attaching the toy to the user.

5. The system of claim 1, wherein the motion sensing device includes a 3-axis accelerometer.

6. The system of claim 1, wherein the voting ensemble includes a J48, a OneR, and a NaiveBayes classifier.

7. The system of claim 1, wherein the voting ensemble is configured to use a function of probabilities.

8. The system of claim 7, wherein the function of probabilities is an average of probabilities.

9. The system of claim 1, wherein at least one of the games includes an avatar, and wherein an attribute of the avatar is modified based on the received activity data.

10. The system of claim 9, wherein at least one of the games includes more than one avatar, and wherein the received activity data is transferable from one avatar to another avatar.

11. The system of claim 1, wherein the computing device is further configured to provide activity data or game information to a social media service.

12. The system of claim 1, wherein the motion sensing device is further configured to refrain from capturing motion data unless a pattern of motion is detected indicative of a user associated with a classifier trained for the motion sensing device.

13. A method of encouraging physical activity, comprising:
  monitoring physical activity of a user to collect motion data using at least one accelerometer;
  analyzing, with a computing device, the motion data to identify one or more physical activities performed by the user, wherein analyzing the motion data includes classifying the motion data as one or more of a plurality of types of physical activity; and
  updating attributes of a video game avatar based on the activities performed by the user;
  wherein updating attributes of a video game avatar includes:
    changing an appearance of the avatar to appear healthy in response to determining that a threshold amount of physical activity has been performed by the user; and
    changing an appearance of the avatar to appear less healthy in response to determining that a predetermined amount of game activity has occurred since the monitored physical activity.

14. The method of claim 13, wherein monitoring physical activity of a user includes collecting motion data using at least one accelerometer located in an accessory coupled to the user.

15. The method of claim 13, wherein the one or more physical activities include at least one of walking, running, climbing up stairs, climbing down stairs, doing jumping jacks, jumping up, long jumping forward, push-ups, swinging a tennis racket, pull-ups, jogging, sleeping, spinning, doing cartwheels, and being carried by a vehicle.

16. The method of claim 13, wherein updating attributes of a video game avatar includes improving an in-game performance of the avatar in response to determining that a threshold amount of physical activity has been performed by the user.

17. The method of claim 13, further comprising:
  retrieving motion data from the at least one accelerometer;
  tagging the motion data as a predetermined type of physical activity; and
  generating a classifier to recognize the predetermined type of physical activity based on motion data.

18. A system for encouraging physical activity, comprising:
  a motion sensing device configured to capture motion data representing a user's physical activity using at least one accelerometer;
  a computing device configured to process motion data captured by the motion sensing device to determine activity data, wherein processing motion data captured by the motion sensing device includes:
    retrieving motion data from the at least one accelerometer of the motion sensing device;
    tagging the motion data as a predetermined type of physical activity;
    generating a classifier to recognize the predetermined type of physical activity based on motion data; and
    classifying motion data captured by the motion sensing device as one or more of a plurality of types of physical activity using the classifier; and
  a computing device configured to:
    receive the activity data; and
    present an interface that includes one or more games for use by the user, wherein one or more attributes of the games are modified based on the received activity data.

* * * * *